United States Defensive Publication [19] (H) [11] T970,006

Rose [43] May 2, 1978

[54] MANUFACTURE OF HALOPHENOLS

[75] Inventor: John Brewster Rose, Letchworth, England

[73] Assignee: Imperial Chemical Industries Limited, London, England

[21] Appl. No.: 812,438

[22] Filed: Jul. 1, 1977

[30] Foreign Application Priority Data

Jul. 9, 1976 United Kingdom ..... 28674/76

[51] Int. Cl.[2] ..... C07C 45/14

[52] U.S. Cl. ..... 260/591; 260/544 D; 260/515 A

[57] ABSTRACT

Halophenols of formula

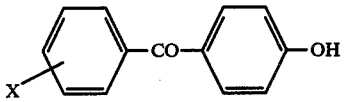

where X = halogen, are made by condensation of a compound

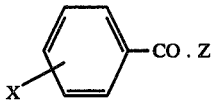

where Z is OH or halogen with a phenol in the presence of anhydrous HF as a catalyst. The compound

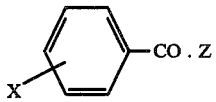

where X = F, may be made in situ by the reaction of

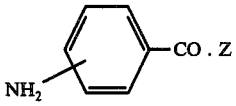

with an alkali metal nitrite in anhydrous HF.

9 Claims, No Sheets Drawing,

8 Pages Specification

The file of this unexamined application may be inspected and copies thereof may be purchased (849 O.G. 1221, Apr. 9, 1968).